United States Patent
Park et al.

(10) Patent No.: US 8,277,217 B2
(45) Date of Patent: Oct. 2, 2012

(54) DENTAL INSTRUMENT FOR CUTTING SOFT TISSUE

(75) Inventors: Kwang Bum Park, Daegu (KR); Kyoung Ho Ryoo, Gwangju (KR)

(73) Assignee: Megagen Implant Co., Ltd. (KR)

( * ) Notice: Subject to any disclaimer, the term of this patent is extended or adjusted under 35 U.S.C. 154(b) by 0 days.

(21) Appl. No.: 13/058,693

(22) PCT Filed: Aug. 11, 2009

(86) PCT No.: PCT/KR2009/004464
§ 371 (c)(1), (2), (4) Date: Feb. 11, 2011

(87) PCT Pub. No.: WO2010/018966
PCT Pub. Date: Feb. 18, 2010

(65) Prior Publication Data
US 2011/0136075 A1   Jun. 9, 2011

(30) Foreign Application Priority Data
Aug. 12, 2008   (KR) .................. 10-2008-0078981

(51) Int. Cl.
*A61C 3/02* (2006.01)
(52) U.S. Cl. ........................................ 433/144; 606/167
(58) Field of Classification Search ................... 433/144, 433/143, 148; 452/137; 128/305.5; 606/84, 606/132, 133, 131, 167, 79; 30/292, 306–307, 30/319
See application file for complete search history.

(56) References Cited

U.S. PATENT DOCUMENTS

| | | | | |
|---|---|---|---|---|
| 2,173,751 A | * | 9/1939 | Burkhart | 30/279.6 |
| 3,636,625 A | * | 1/1972 | Pracht | 30/26 |
| 3,683,892 A | * | 8/1972 | Harris | 600/567 |
| 3,688,407 A | * | 9/1972 | Paquette et al. | 433/144 |
| 3,797,505 A | * | 3/1974 | Gilhaus et al. | 132/76.4 |

(Continued)

FOREIGN PATENT DOCUMENTS

KR   10-0798683   1/2008

(Continued)

OTHER PUBLICATIONS

European Search Report—European Application No. EP 09 80 6828 dated Jan. 5, 2012.

(Continued)

*Primary Examiner* — Cris L Rodriguez
*Assistant Examiner* — Matthew Saunders
(74) *Attorney, Agent, or Firm* — Cantor Colburn LLP

(57) ABSTRACT

Disclosed is a dental instrument for cutting soft tissue. The dental instrument for cutting soft tissue according to the present invention includes: a main body having an inlet portion for inserting soft tissue to be cut into the main body; a cutter blade arranged in the main body such that at least a part of the cutter blade is exposed outwardly through the inlet portion; and a lid for covering the upper portion of the main body. The cutter blade includes a first cutter blade having a first cut depth, and a second cutter blade arranged in the vicinity of the first cutter blade, and which has a second cut depth shallower than the first cut depth. The dental instrument of the present invention makes it possible to cut the soft tissue in the deep part of a mouth in an easy and simple process, thereby improving the convenience of soft tissue implantation.

10 Claims, 4 Drawing Sheets

U.S. PATENT DOCUMENTS

| | | | | |
|---|---|---|---|---|
| 4,098,278 A | * | 7/1978 | Schwartz | 606/132 |
| 4,221,222 A | | 9/1980 | Detsch | |
| 4,665,915 A | * | 5/1987 | Grollimund | 606/132 |
| 5,330,495 A | * | 7/1994 | Dettwiler et al. | 606/167 |
| 5,601,584 A | * | 2/1997 | Obagi et al. | 606/172 |
| 5,830,225 A | * | 11/1998 | Detsch | 606/167 |
| 6,264,668 B1 | * | 7/2001 | Prywes | 606/167 |
| 6,440,143 B2 | * | 8/2002 | Kasten | 606/132 |
| 6,887,250 B1 | * | 5/2005 | Dority et al. | 606/132 |
| 2001/0047177 A1 | * | 11/2001 | Kasten | 606/132 |
| 2006/0229648 A1 | * | 10/2006 | Dan | 606/166 |
| 2010/0234849 A1 | * | 9/2010 | Bouadi | 606/84 |

FOREIGN PATENT DOCUMENTS

| | | |
|---|---|---|
| KR | 100798683 | 1/2008 |
| WO | 2007/106740 | 9/2007 |
| WO | 2008/136004 | 11/2008 |

OTHER PUBLICATIONS

International Search Report—PCT/KR2009/004464 dated Feb. 24, 2010.

* cited by examiner

DENTAL INSTRUMENT FOR CUTTING SOFT TISSUE

TECHNICAL FIELD

The inventive concept relates to a dental instrument, and more particularly, to a dental instrument for cutting soft tissue in the oral cavity to provide soft tissue used for a soft tissue transplantation surgery.

BACKGROUND ART

In general, a biomaterial may be divided into hard tissue and soft tissue. Bones or teeth are examples of the hard tissue. Skin, blood vessels, cartilages, or ligaments are examples of the soft tissue. The hard tissue has an elastic coefficient and a tensile strength that are higher than those of the soft tissue.

The soft tissue as a biomaterial has been used in the field of dental treatment. In particular, soft tissue transplantation surgeries have been widely used as a method for rebuilding or treating damaged soft tissues during a dental surgery such as implant surgery.

In case of an implant surgery that is recently in the limelight, gums around an implant need to be healthy so that a tooth implant may be used for a long time. This is the same principle that is used for a case in which a flag driven into sands. The flag does not fall when a large amount of sand exists around the flag. That is, even when an alveolar bone firmly holds the root of a tooth, the tooth may sway when the gum surrounding the tooth is insufficient. Also, exposed nerves may cause pain and it is not aesthetic. In this case, a soft tissue transplantation surgery is needed.

To transplant soft tissues to an area where the thickness of a gum is thin or the gum is lost, soft tissue to be transplanted needs to be primarily obtained. To this end, soft tissues in an amount needed for transplantation are cut off from other normal area in the oral cavity. Typically, soft tissues in the palate of the oral cavity are used because the flesh of the palate is relatively thicker than that of other places.

Dental instruments for cutting soft tissue are used to cut the soft tissue off from the oral cavity to provide soft tissue used for a soft tissue transplantation surgery.

A conventional dental instrument for cutting soft tissue may include a main body equipped with a blade, a cover covering the upper portion of the main body, and a handle coupled to the main body and held by an operator. The blade is coupled to the main body by being separated therefrom to have a predetermined cutting depth. Also, the main body and the cover may be formed in a single body.

In the meantime, soft tissue cut including the outer surface of a particular portion in the oral cavity may be used as the soft tissue to be transplanted in a portion having a thin thickness or in a place where gum is lost. However, it is advantageous to use soft tissue arranged at a predetermined depth under the outer surface of the particular portion in the oral cavity because of a high transplantation success rate.

Since the conventional dental instrument for cutting soft tissue is equipped with a single blade having a predetermined cutting depth, to cut soft tissue arranged at a predetermined depth under the outer surface of the particular portion in the oral cavity, soft tissue is primarily cut by a predetermined depth under the outer surface and secondarily soft tissue by a desired thickness is cut off from the portion where the outer surface is removed.

In addition, the cutting depth of a blade installed at a dental instrument for cutting soft tissue used for the first cutting process is different from that of a blade installed at a dental instrument for cutting soft tissue used for the second cutting process. Thus, two or more dental instruments for cutting soft tissue are needed for cutting soft tissue. Furthermore, when a single dental instrument for cutting soft tissue is in use, it is inconvenient to replace the blade for each process.

DETAILED DESCRIPTION OF THE INVENTION

Technical Problem

The inventive concept provides a dental instrument for cutting soft tissue which may easily and simply cut soft tissue arranged at a predetermined depth under the outer surface in the oral cavity so that a soft tissue transplantation surgery may be facilitated.

Advantageous Effects

According to the present inventive concept, since the dental instrument for cutting soft tissue employs a dual blade structure of the first and second blades having different cutting depths, the soft tissue arranged at a predetermined depth under the outer surface in the oral cavity may be easily and simply cut so that a soft tissue transplantation surgery may be facilitated.

BEST MODE FOR CARRYING OUT THE INVENTION

Figure 1:
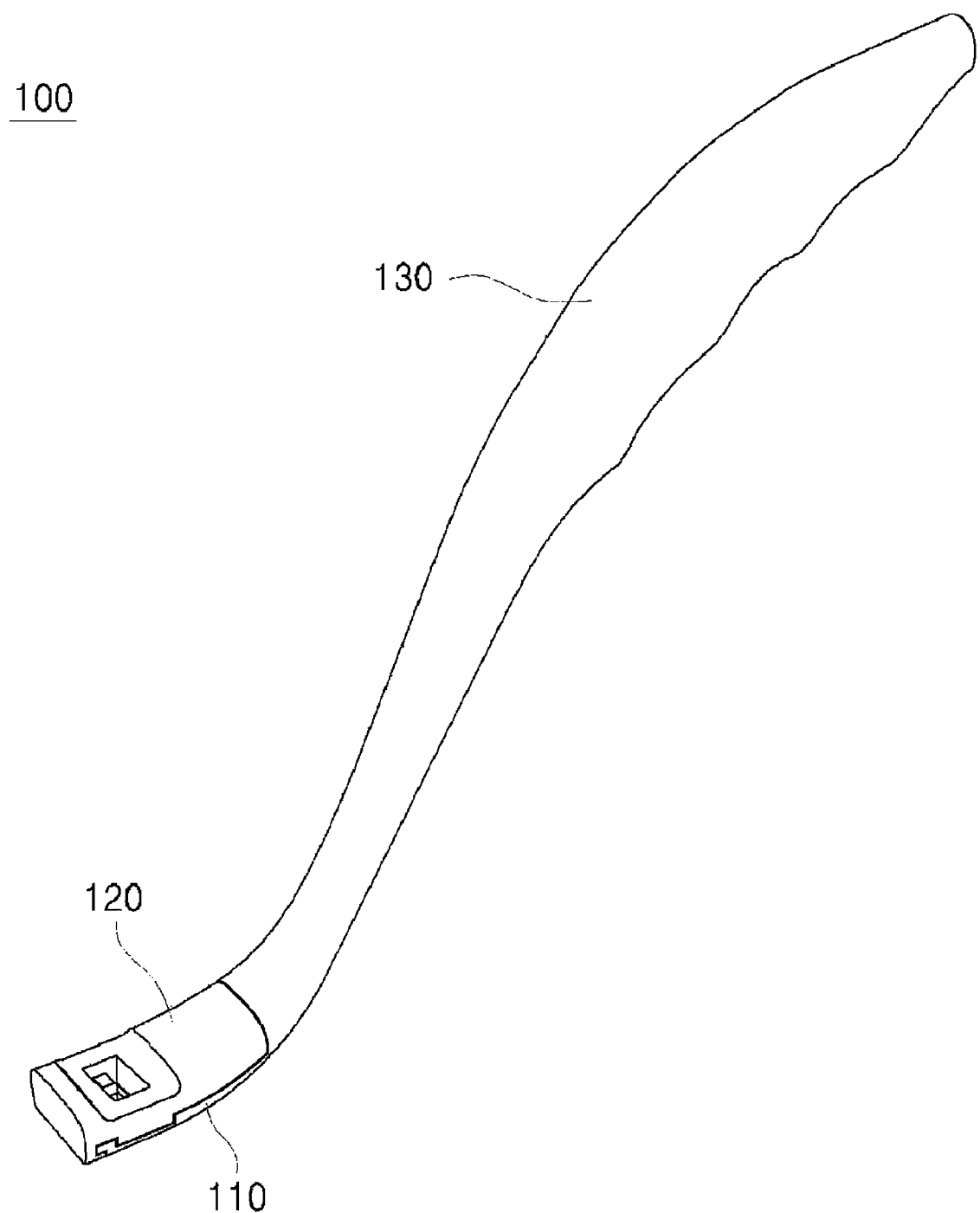
FIG. 1 illustrates the structure of a plasma processing apparatus according to an embodiment of the present invention.

According to an aspect of the inventive concept, there is provided a dental instrument for cutting soft tissue, which includes a main body in which an inlet hole through which cut soft tissue is input is formed, a blade provided at the main body, at least a portion of the blade being exposed to the outside through the inlet hole, and a cover covering an upper portion of the main body, wherein the blade includes a first blade having a first cutting depth, and a second blade provided adjacent to the first blade and having a second cutting depth smaller than the first cutting depth.

The second blade may be arranged in front of the first blade with respect to a cutting direction.

Each of the first and second blades may include a cutting portion where a blade surface is formed and exposed to the outside through the inlet hole, and a pair of wing portions bent and extending from both ends of the cutting portion and supported by the main body in the main body.

To fix the position of the blade in the main body, a position fixing hole may be formed in each of the wing portions and a position fixing protrusion inserted in the position fixing hole may be formed in the main body.

A position fixing recess engaged with the position fixing protrusion may be formed in the cover.

An exhaust hole through which soft tissue input through the inlet hole is exhausted may be formed in the cover.

A guide wall extending toward the inlet hole may be provided at a position adjacent to the exhaust hole to guide the soft tissue input through the inlet hole to the exhaust hole.

The guide wall may be inclined with respect to a center line of the exhaust hole.

A blade installation portion recessively formed in an area including the inlet hole may be provided at the main body, and a protruding portion protruding from an area including the exhaust hole to be engaged with the blade installation portion may be provided at the cover.

The first and second blades may be either separately or integrally formed.

The blade may be manufactured separately from the main body and coupled to the main body.

The blade may be formed of metal and the main body is formed of plastic, and the blade may be integrally formed at the main body by injection molding.

MODE FOR CARRYING OUT THE INVENTION

The attached drawings for illustrating embodiments of the inventive concept are referred to in order to gain a sufficient understanding of the inventive concept and the merits thereof.

Hereinafter, the inventive concept will be described in detail by explaining embodiments of the inventive concept with reference to the attached drawings. Like reference numerals in the drawings denote like elements.

Figure 2:
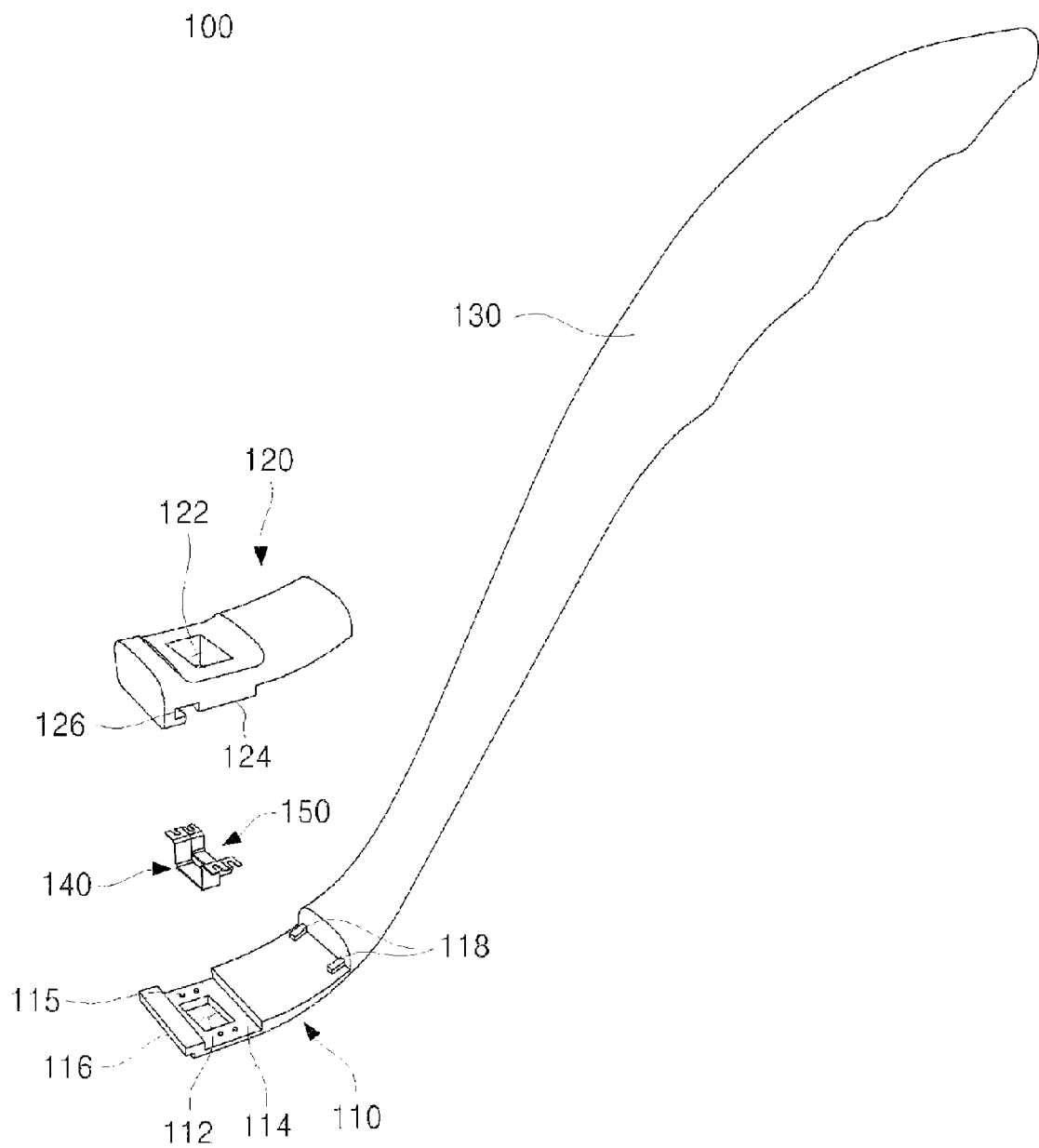
FIG. 2 is a perspective view of a gate value of FIG. 1.
Figure 3:
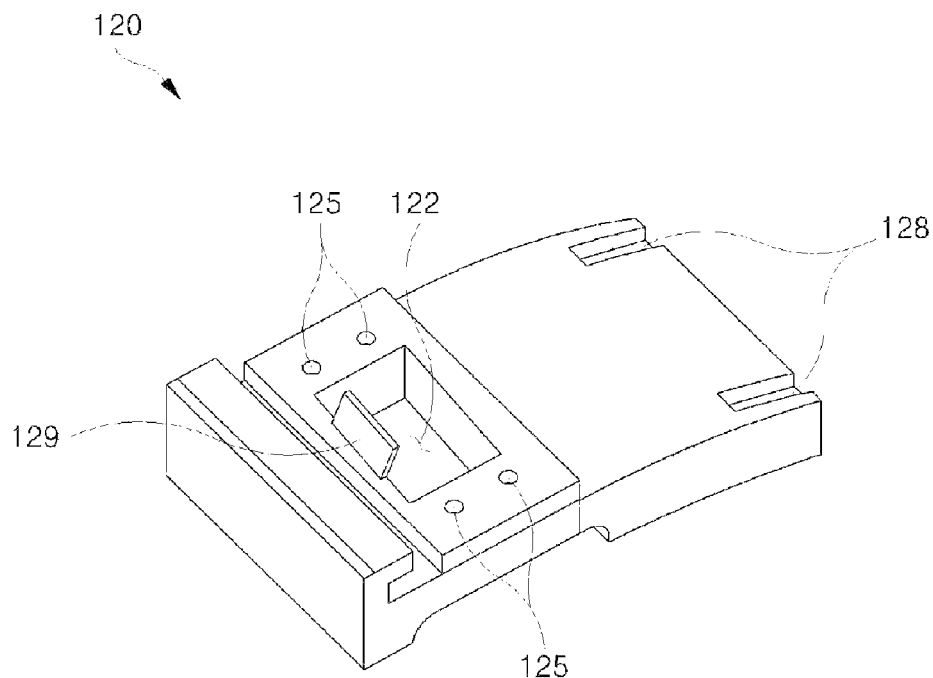
FIG. 3 is a partially cut perspective view of the gate valve taken along line III-III of FIG. 2.
Figure 4:
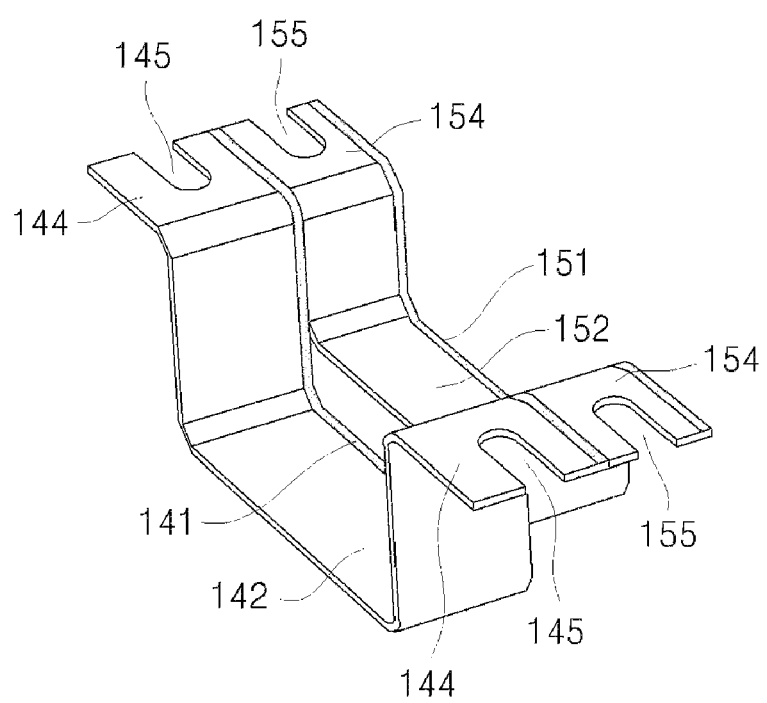
FIG. 4 is a perspective view of a cylinder of FIG. 2 during a normal operation.
Figure 5:
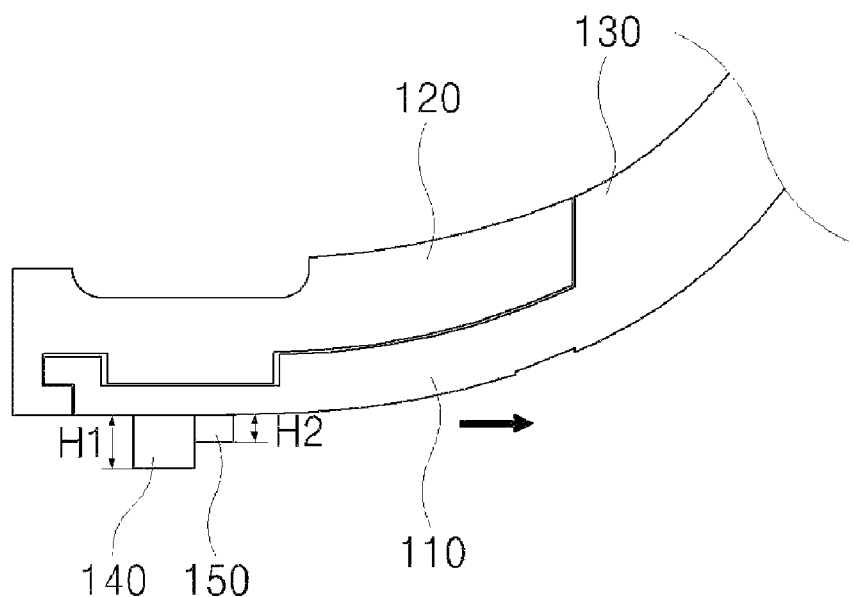
FIG. 5 is a perspective view of a cylinder of FIG. 2 during a maintenance and repair operation.
Figure 6:
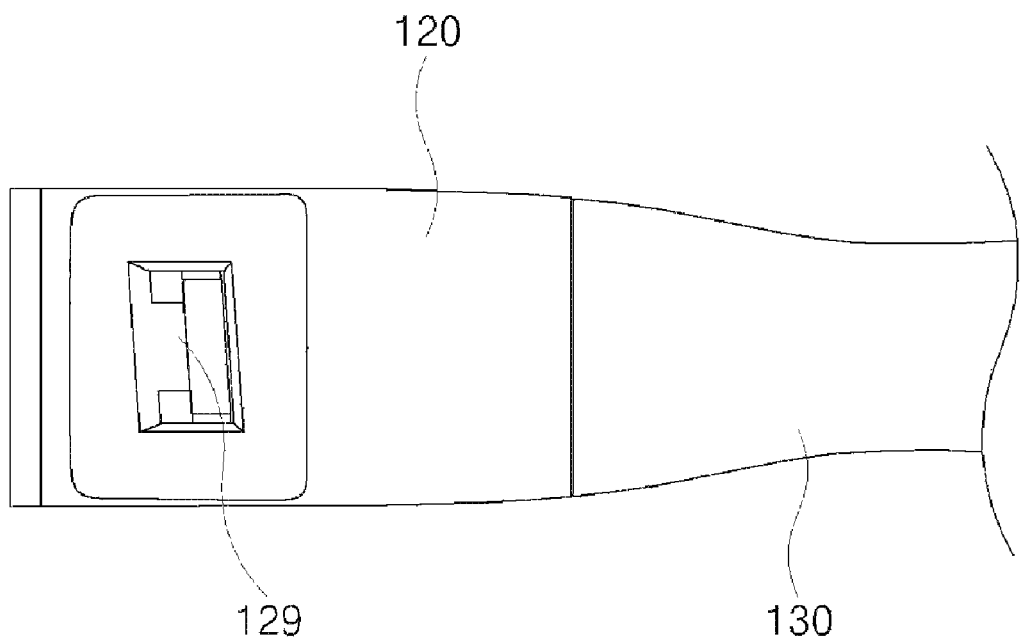
FIG. 6 is a perspective view of a locking pin of FIG. 4

FIG. 1 is a perspective view of a dental instrument for cutting soft tissue according to an exemplary embodiment of the present inventive concept. FIG. 2 is an exploded perspective view of the dental instrument for cutting soft tissue of FIG. 1. FIG. 3 is a rear perspective view of the cover of FIG. 2. FIG. 4 is an enlarged perspective view of the blade of FIG. 2. FIG. 5 is a side view illustrating a portion of the dental instrument for cutting soft tissue of FIG. 1. FIG. 6 is a plan view of the dental instrument for cutting soft tissue of FIG. 1.

Referring to FIGS. 1 and 2, a dental instrument 100 for cutting soft tissue (hereinafter, referred to as the dental instrument) according to an exemplary embodiment of the present inventive concept is a dental instrument for cutting soft tissue in the oral cavity, mainly, the soft tissue of the palate, to provide soft tissue used for a soft tissue transplantation surgery. The dental instrument 100 may include a main body 110 having blades 140 and 150 for cutting soft tissue in the oral cavity, a cover 120 covering the upper portion of the main body 110, and a handle 130 extending long from the main body 110 to be held by an operator.

In the present exemplary embodiment, the main body 110, the cover 120, and the handle 130 are formed of plastic that may be injection molded in consideration of manufacturing convenience and lightness. However, the material of the main body 110, the cover 120, and the handle 130 of the dental instrument according to the present inventive concept is not limited to plastic and other material such as metal may be used therefor.

Referring to FIGS. 1-6, an inlet hole 112 for guiding soft tissue cut by the blades 140 and 150 is formed in the main body 110 of the dental instrument 100. A blade installation portion 114 in which the blades 140 and 150 are installed is recessively formed in an area including the inlet hole 112. The blades 140 and 150 are installed at the blade installation portion 114 such that the center portions of the blades 140 and 150 may be exposed to the outside through the inlet hole 112.

The cover 120 of the dental instrument 100 is coupled to the main body 110 to cover the upper portion of the main body 110. An exhaust hole 122 through which soft tissue input through the inlet hole 112 of the main body 110 is exhausted is formed in the cover 120. In the present exemplary embodiment, the cover 120 is coupled to the main body 110 in a forced fit. To this end, a hook groove 126 formed at the leading end of the cover 120 is engaged with a hook step 116 formed at the leading end of the main body 110. Also, a pair of insertion holes 128 in which a pair of insertion protrusions 118 formed at the rear end of the main body 110 are inserted are provided at the rear end of the cover 120. An adhesive may be coated between the lower surface of the cover 120 and the upper surface of the main body 110 for a more firm coupling therebetween.

However, in the present inventive concept, the coupling method between the cover 120 and the main body 110 is not limited to the above description and a variety of methods may be adopted instead. For example, the cover 120 may be hinge coupled to the main body 110 to open or close the upper portion of the main body 110. In this case, the exhaust hole 122 through which soft tissue input through the inlet hole 112 of the main body 110 is exhausted may be omitted.

That is, when the cover 120 is coupled to the main body 110 to open and close the upper portion of the main body 110, a space defined by the main body 110 and the cover 120 may accommodate the cut soft tissue. Accordingly, even when the exhaust hole 122 is not formed in the cover 120, the cut soft tissue may be taken out by opening the cover 120. In addition, the cover 120 and the main body 110 may be integrally manufactured by injection molding.

A protruding portion 124 protrudes from an area including the exhaust hole 122 to be engaged with the blade installation portion 114 of the main body 110, as illustrated in FIGS. 2 and 3. The protruding portion 124 of the cover 120 fixes the blades 140 and 150 by pressing both ends of the blades 140 and 150 installed at the blade installation portion 114. Accordingly, the blades 140 and 150 may be stably fixed in the main body 110 so that movements particularly in upward and downward directions may be prevented.

Also, a guide wall 129 is provided at the lower surface of the cover 120 by extending from a position adjacent to the leading end of the exhaust hole 122 toward the inlet hole 112 of the main body 110, as illustrated in FIGS. 3 and 6. The guide wall 129 guides the soft tissue input through the inlet hole 112. The guide wall 129 is inclined with respect to the center line of the exhaust hole 122, as illustrated in FIG. 3. This is to facilitate the delivery of the cut soft tissue input through the inlet hole 112 to the exhaust hole 122. Also, the guide wall 129 extends toward a position adjacent to the blades 140 and 150 exposed to the outside through the inlet hole 112. This is to prevent the input of the soft tissue cut by the blades 140 and 150 through the inlet hole 112 and the escape of the soft tissue between the blades 140 and 150 and the lower surface of the main body 110.

Referring to FIGS. 1 and 2, the handle 130 of the dental instrument 100 is a portion held by an operator during the cutting of the soft tissue in the oral cavity. The handle 130 is formed of the same plastic material as that used for the main body 110 and integrally formed with the main body 110. In the present inventive concept, however, the handle 130 may be coupled to the main body 110 to be detachable in a screw coupling method, unlike the present exemplary embodiment.

Referring to FIGS. 2-5, the blades 140 and 150 installed at the main body 110 have a dual blade structure including the first blade 140 and the second blade 150 arranged adjacent to the first blade 140. Both of the first and second blades 140 and 150 are formed of metal. The second blade 150 is arranged in front of the first blade 140 with respect to a cutting direction along an arrow of FIG. 5. That is, with respect to the leading end of the main body 110, the second blade 150 is arranged behind the first blade 140.

The first and second blades 140 and 150 respectively include cutting portions 142 and 152 exposed to the outside through the inlet hole 112 and having blade surfaces 141 and 151, and a pair of wing portions 144 and 154 bent and extending from both ends of the butting portions 142 and 152 and supported by the blade installation portion 114 in the main body 110.

The cutting portions 142 and 152 are portions where the blade surfaces 141 and 151 are formed with respect to the cutting direction and have a shape of "⌐" to be exposed to the outside through the inlet hole 112. Also, the wing portions 144 and 154 are coupled to the main body 110 and horizontally bent and extending from both ends of the cutting portions 142 and 152 that are vertical to the lower surface of the main body 110. The wing portions 144 and 154 are placed and supported on the blade installation portion 114 by being inserted in the main body 110 via the inlet hole 112. The wing portions 144 and 154 placed and supported on the blade installation portion 114 are pressed and fixed by the protruding portion 124 of the cover 120 as described above. The blade surfaces 141 and 151 are inclined at a predetermined angle with respect to the cutting direction, as illustrated in FIG. 3. This is to improve the cutting performance of the blade surfaces 141 and 151.

The first and second blades 140 and 150 having the above-described structure have a dual blade structure having different cutting depths H1 and H2. That is, the cutting portion 142 of the first blade 140 is exposed to the outside through the inlet hole 112 so that the first blade 140 may have the first cutting depth H1. The cutting portion 152 of the second blade 150 is exposed to the outside through the inlet hole 112 so that the second blade 150 may have the second cutting depth H2. The cutting depth denotes a distance from the lower surface of the main body 110 to the blade surface 141 or 151, which determines the thickness of the soft tissue cut during the soft tissue cutting.

As described above, the soft tissue transplantation surgery in the dental field denotes a surgery of cutting a desired amount of soft tissue off from a particular portion, mainly, the palate, in the oral cavity, and transplant the cut soft tissue in a gum, when the thickness of a gum around a portion where an implant is placed is thin or the gum is insufficient. Although the cut soft tissue including the outer surface of the particular portion in the oral cavity may be used as soft tissue to be transplanted in the gum that is thin or lost, soft tissue arranged at a predetermined depth under the outer surface of the particular portion in the oral cavity is used because of its high transplantation success rate.

However, since a conventional dental instrument for cutting soft tissue is equipped with a single blade having a predetermined cutting depth, to cut soft tissue arranged at a predetermined depth under the outer surface of the particular portion in the oral cavity, soft tissue at a predetermined depth under the outer surface is primarily cut and secondly soft tissue of a desired thickness is cut off from a portion where the outer surface is removed. These processes are inconvenient.

Also, since the cutting depths of a blade installed at a dental instrument used for the first cutting process and a blade installed at a dental instrument used for the second cutting process are different from each other, two or more dental instruments are needed for cutting the soft tissues in the soft tissue cutting processes. Furthermore, when a single dental instrument is used to cut soft tissue, it is inconvenient to replace the blade for each process.

To solve the above inconvenience generated when the conventional dental instrument is in use, the dental instrument 100 according to the present exemplary embodiment has a dual blade structure of the first blade 140 and the second blade 150 having the different cutting depths H1 and H2 so that the soft tissue transplantation surgery may be facilitated.

That is, in the dental instrument 100 according to the present exemplary embodiment, since the second blade 150 having the cutting depth H2 smaller than the cutting depth H1 of the first blade 140 is arranged in front of the first blade 140 with respect to the cutting direction, the soft tissue arranged at a predetermined depth under the outer surface of the particular portion in the oral cavity may be cut in a single cutting process.

In detail, when an operator cuts soft tissue off from the particular portion in the oral cavity using the dental instrument 100 according to the present exemplary embodiment, the soft tissue is cut by the first blade 140 to a thickness corresponding to the second cutting depth H2 off from the outer surface of the particular portion. The upper and lower surfaces of the soft tissue arranged at a predetermined depth under the outer surface of the particular portion are respectively cut by the second blade 150 and the first blade 140 so that the cut soft tissue is input between the first and second blades 140 and 150.

Accordingly, when soft tissue is cut off from the particular portion in the oral cavity by using the dental instrument 100 according to the present exemplary embodiment, the soft tissue arranged at a predetermined depth under the outer surface of the particular portion in the oral cavity may be cut by using a dental instrument equipped with blades having different cutting depths or by not replacing the blade.

The first and second blades 140 and 150 may be installed separately, but close to each other, at the blade installation portion 114 of the main body 110. Alternatively, the first and second blades 140 and 150 may be integrally formed and installed at the blade installation portion 114 of the main body 110. The first and second blades 140 and 150 may be manufactured by performing cutting and bending processes to a blade having a long plate shape. In terms of manufacturing convenience, the first and second blades 140 and 150 may be separately formed. In terms of assembly convenience and stability, the first and second blades 140 and 150 may be integrally formed. Also, when the first and second blades 140 and 150 are separately formed, the first and second blades 140 and 150 are installed at the main body 110 by being in contact with each other or slightly separated from each other.

Also, as described above, the positions of the first and second blades 140 and 150 may be fixed in the main body 110 as the blade installation portion 114 recessively formed in the main body 110 and the protruding portion 124 protruding from the cover 120 are pressed to contact each other with the wing portions 144 and 154 of the first and second blades 140 and 150 interposed therebetween. For more firm position fixing, in the present exemplary embodiment, position fixing holes 145 and 155 are formed in the wing portions 144 and 154 of the first and second blades 140 and 150 and position fixing protrusions 115 inserted in the position fixing holes 145 and 155 are formed on the blade installation portion 114 of the main body 110. Also, position fixing recesses 125 engaged with the position fixing protrusions 115 are formed in the protruding portion 124 of the cover 120.

In the present exemplary embodiment in which the first and second blades 140 and 150 are separately formed, the position fixing holes 145 and 155 are respectively formed at the first and second blades 140 and 150. Accordingly, the position fixing protrusions 115 and the position fixing recesses 125 are respectively formed at four positions of each of the blade installation portion 114 and the protruding portion 124. In the present inventive concept, the shape, position, and number of the position fixing protrusions and the position fixing holes are not limited to the above descriptions.

Accordingly, the positions of the first and second blades 140 and 150 are stably fixed in the main body 110. In particular, the first and second blades 140 and 150 may be prevented from being twisted at the fixed positions during the cutting of soft tissue. In addition, according to the above-described blade position fixing structure according to the present exemplary embodiment, the determination of the positions of the first and second blades 140 and 150 in the process of assembling the first and second blades 140 and 150 and the cover 120 to the main body 110 is made easy so that assembly convenience may be improved.

Also, in the present exemplary embodiment, the first and second blades 140 and 150 formed of metal are manufactured separately from the main body 110 formed of plastic. However, the first and second blades 140 and 150 formed of metal may be integrally formed by injection molding with the main body 110 formed of plastic. That is, the coupling method of the first and second blades 140 and 150 and the main body 110 is not limited to the above-described method.

As described above, according to the present inventive concept, since the dental instrument for cutting soft tissue employs a dual blade structure of the first and second blades having different cutting depths, the soft tissue arranged at a predetermined depth under the outer surface in the oral cavity may be easily and simply cut so that a soft tissue transplantation surgery may be facilitated.

While the inventive concept has been particularly shown and described with reference to exemplary embodiments thereof, it will be understood that various changes in form and details may be made therein without departing from the spirit and scope of the following claims.

INDUSTRIAL APPLICABILITY

The present inventive concept can be applied to the technical field of a dental instrument for cutting soft tissue in the oral cavity.

The invention claimed is:

1. A dental instrument for cutting soft tissue, the dental instrument comprising:
   a main body having an inlet hole through which cut soft tissue is input;
   a blade provided at the main body, at least a portion of the blade protruding to an outside through the inlet hole to define a cutting depth according to a protruding length; and
   a cover covering an upper portion of the main body,
   wherein the blade comprises:
      a first blade having a first protruding length defining a first cutting depth; and
      a second blade having a second protruding length defining a second cutting depth, the first and second blades being disposed adjacent to each other and in a row along a cutting direction, the second protruding length being smaller than the first protruding length, thereby defining the second cutting depth to be smaller than the first cutting depth,
   wherein the cover has an exhaust hole through which the soft tissue input through the inlet hole is exhausted, and
   wherein a blade installation portion recessively formed in an area including the inlet hole is provided at the main body, and a protruding portion protruding from an area including the exhaust hole to be engaged with the blade installation portion is provided at the cover.

2. The dental instrument of claim 1, wherein the second blade is arranged in front of the first blade with respect to the cutting direction.

3. The dental instrument of claim 2, wherein each of the first and second blades comprises:
   a cutting portion where a blade surface is formed and protruded to the outside through the inlet hole; and
   a pair of wing portions bent and extending from both ends of the cutting portion and supported by the main body.

4. The dental instrument of claim 3, wherein a position fixing hole is formed in each of the wing portions and a position fixing protrusion to be inserted into the position fixing hole is formed in the main body.

5. The dental instrument of claim 4, wherein a position fixing recess to be engaged with the position fixing protrusion is formed in the cover.

6. The dental instrument of claim 1, wherein a guide wall extending toward the inlet hole is provided at a position adjacent to the exhaust hole to guide the soft tissue input through the inlet hole to the exhaust hole.

7. The dental instrument of claim 6, wherein the guide wall is inclined with respect to a center line of the exhaust hole.

8. The dental instrument of claim 1, wherein the first and second blades are separately or integrally formed.

9. The dental instrument of claim 1, wherein the blade is manufactured separately from the main body and coupled to the main body.

10. The dental instrument of claim 1, wherein the blade is formed of metal and the main body is formed of plastic, and the blade is integrally formed at the main body by injection molding.

* * * * *